(12) United States Patent
Guyette

(10) Patent No.: US 9,656,037 B2
(45) Date of Patent: May 23, 2017

(54) NASAL MASK

(76) Inventor: Robert F. Guyette, Scottsdale, AZ (US)

( * ) Notice: Subject to any disclaimer, the term of this patent is extended or adjusted under 35 U.S.C. 154(b) by 248 days.

(21) Appl. No.: 13/808,127

(22) PCT Filed: Jul. 7, 2011

(86) PCT No.: PCT/US2011/043177
§ 371 (c)(1),
(2), (4) Date: Jan. 3, 2013

(87) PCT Pub. No.: WO2012/006415
PCT Pub. Date: Jan. 12, 2012

(65) Prior Publication Data
US 2013/0109992 A1    May 2, 2013

Related U.S. Application Data

(60) Provisional application No. 61/362,386, filed on Jul. 8, 2010.

(51) Int. Cl.
| | |
|---|---|
| *A61M 16/06* | (2006.01) |
| *A62B 18/02* | (2006.01) |
| *A61M 16/12* | (2006.01) |
| *A61B 5/08* | (2006.01) |
| *A61B 5/097* | (2006.01) |
| *A61M 16/10* | (2006.01) |
| *A61M 16/00* | (2006.01) |

(52) U.S. Cl.
CPC ......... *A61M 16/0666* (2013.01); *A61B 5/082* (2013.01); *A61B 5/097* (2013.01); *A61M 16/0057* (2013.01); *A61M 16/06* (2013.01); *A61M 16/0672* (2014.02); *A61M 16/104* (2013.01); *A61M 16/12* (2013.01); *A61M 16/009* (2013.01); *A61M 2202/0208* (2013.01); *A61M 2202/0283* (2013.01); *A61M 2230/432* (2013.01); *Y02C 20/10* (2013.01)

(58) Field of Classification Search
CPC .. A61M 2016/0616; A61M 2210/0618; A61M 16/06–16/0694; A61M 2016/0661; A62B 27/00; A62B 27/14; A62B 18/00–18/88; A62B 7/00; A62B 7/14
USPC ............ 128/200.24, 203.12, 205.25, 206.21, 128/206.24, 206.25, 207.11, 207.13, 128/207.18
See application file for complete search history.

(56) References Cited

U.S. PATENT DOCUMENTS

| | | | | |
|---|---|---|---|---|
| 4,106,505 A | * | 8/1978 | Salter et al. ............. | 128/207.18 |
| 4,248,218 A | * | 2/1981 | Fischer ............ | A61M 16/0666 |
| | | | | 128/204.18 |

(Continued)

*Primary Examiner* — Peter S Vasat
*Assistant Examiner* — Ned T Heffner
(74) *Attorney, Agent, or Firm* — Cahill Glazer PLC

(57) ABSTRACT

A surgical mask for use in dental procedures, and oral or facial surgery, formed of a continuous sheet of flexible material comprising a nose-conforming shell incorporating adhesive material for sealing and for maintaining position on the patient during the dental or surgical procedure. The mask forms an encasement for input/output manifolds, and terminates in flexible flange at the columella-labial junction; the mask includes a manifold for receiving and directing $N_2O/O_2$ into the nasal vault of the patient, and for the removal of exhalant and the scavenging of gases from the work area.

6 Claims, 3 Drawing Sheets

REAR VIEW

(56) References Cited

U.S. PATENT DOCUMENTS

| | | |
|---|---|---|
| 4,454,880 A | 6/1984 | Muto et al. |
| 4,846,170 A | 7/1989 | McAnalley et al. |
| 5,137,017 A | 8/1992 | Salter |
| 5,474,060 A * | 12/1995 | Evans ...................... 128/204.22 |
| 5,658,270 A * | 8/1997 | Lichstein ...................... 604/387 |
| 5,676,133 A * | 10/1997 | Hickle et al. ............ 128/205.12 |
| 5,901,705 A | 5/1999 | Leagre |
| 6,016,801 A | 1/2000 | Philips |
| 6,129,082 A | 10/2000 | Leagre |
| 6,439,234 B1 | 8/2002 | Curti et al. |
| 6,561,193 B1 | 5/2003 | Noble |
| 6,584,977 B1 | 7/2003 | Serowski |
| 6,637,434 B2 | 10/2003 | Noble |
| 6,655,385 B1 | 12/2003 | Curti et al. |
| 6,694,973 B1 | 2/2004 | Dunhao et al. |
| 6,848,446 B2 | 2/2005 | Noble |
| 7,047,969 B2 | 5/2006 | Noble |
| 7,178,521 B2 | 2/2007 | Burrow et al. |
| 7,178,524 B2 | 2/2007 | Noble |
| 7,201,168 B2 | 4/2007 | McGrail et al. |
| 7,243,649 B2 | 7/2007 | Moenning et al. |
| 7,481,217 B2 | 1/2009 | Milles |
| 7,500,482 B2 | 3/2009 | Biederman |
| 7,753,051 B2 | 7/2010 | Burrow et al. |
| 2008/0223375 A1 * | 9/2008 | Cortez .............. A61M 16/0672 128/207.18 |

* cited by examiner

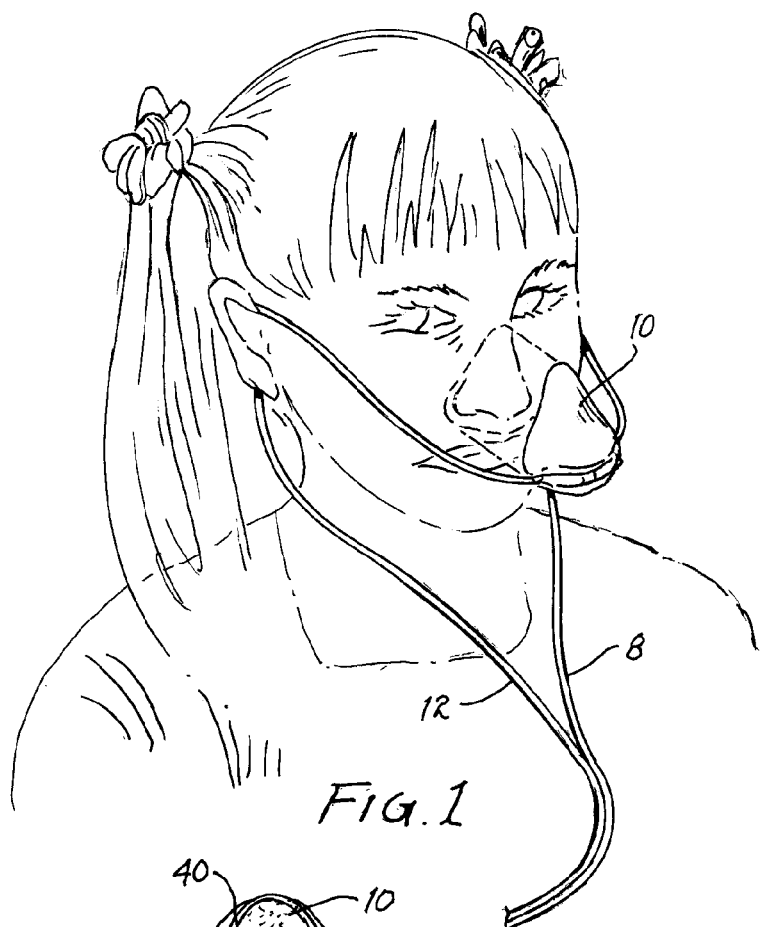
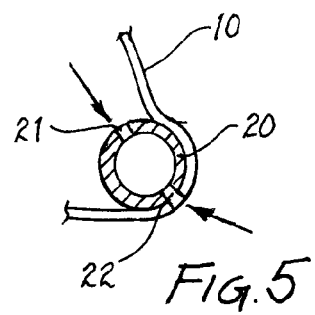
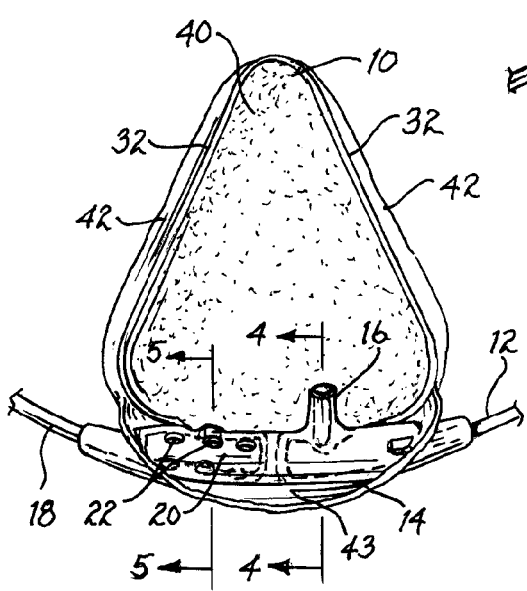
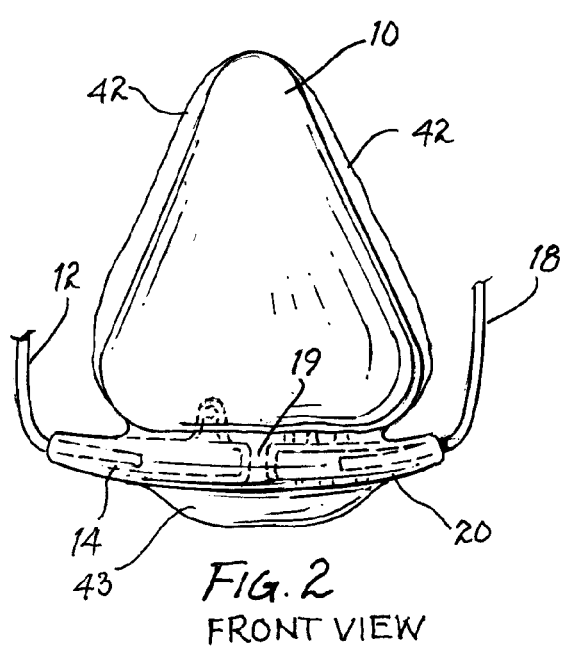

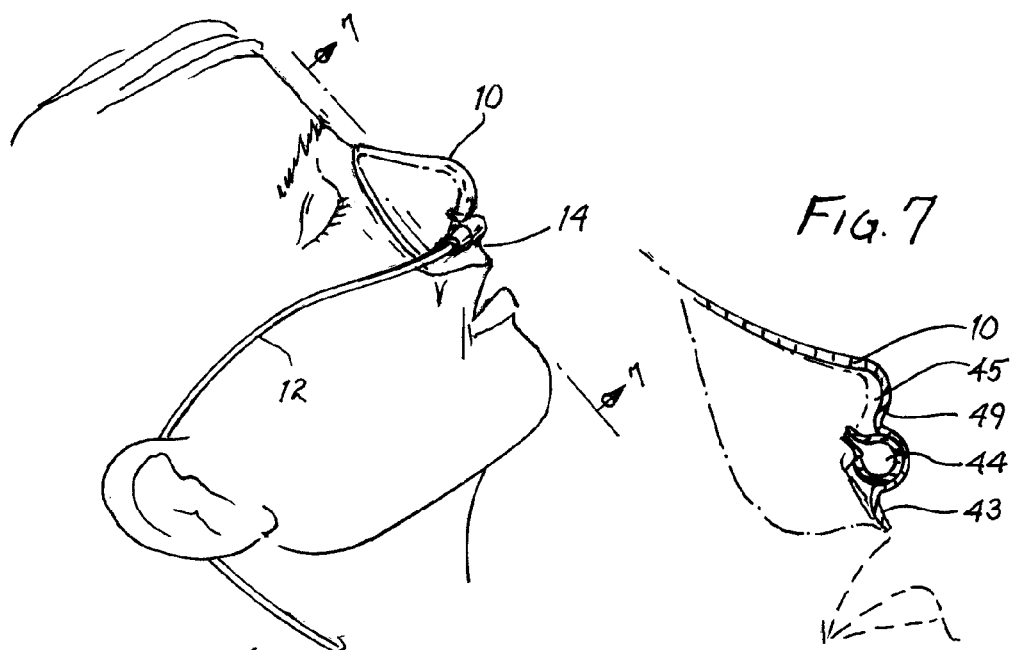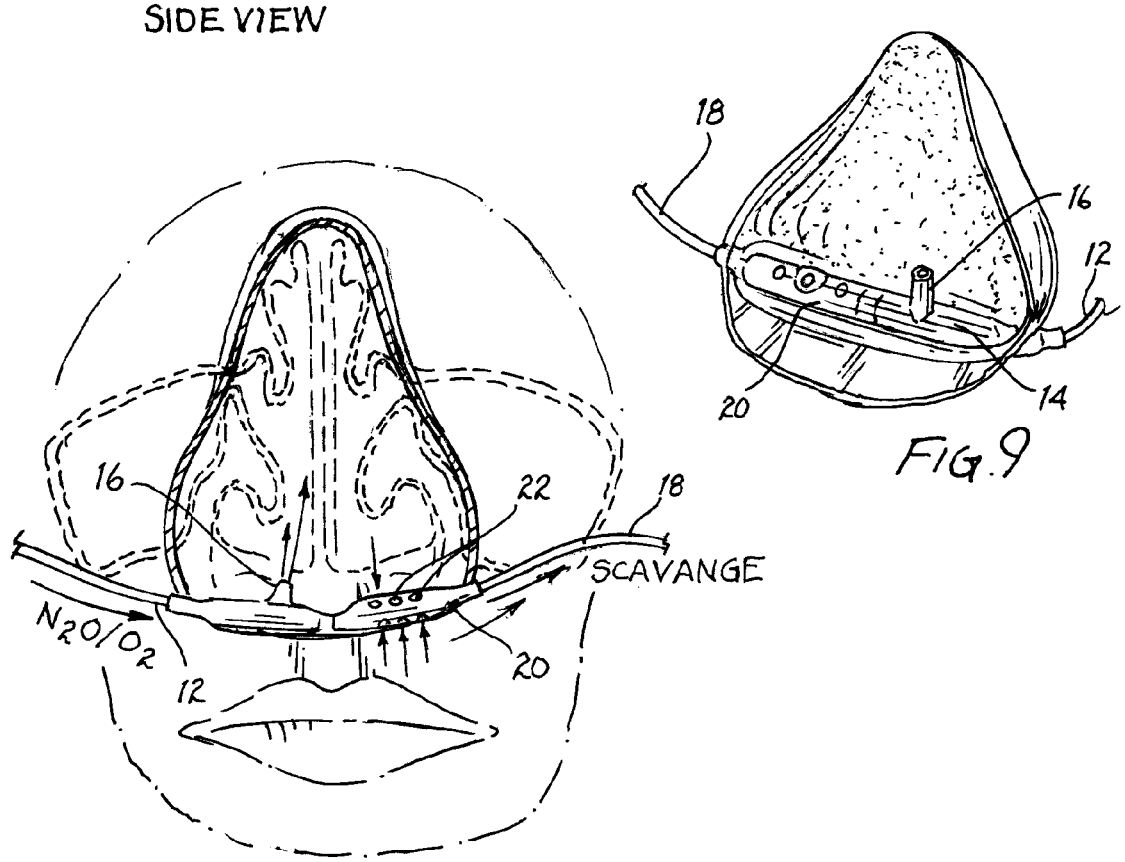

NASAL MASK

CROSS-REFERENCE TO RELATED APPLICATIONS

This application is related to and claims priority to a provisional application entitled "NASAL MASK" filed Jul. 8, 2010, and assigned Ser. No. 61/362,386.

FIELD OF THE INVENTION

The present invention relates to the administration of nitrous oxide/oxygen mixture for delivery to a patient during dental treatment, oral surgery or facial surgery.

BACKGROUND OF THE INVENTION

For many dental, oral surgery and facial surgery procedures, the administration of a nitrous oxide/oxygen mixture may be desirable. The nitrous oxide/oxygen mixture is administered as an analgesic and relaxant for the patient. The mixture is delivered to the patient through a mask that directs the mixture to the patient but must allow unobstructed access to the surgical area. During such procedures, it is therefore important to prevent or minimize intrusion into the surgical area; any mask utilized for the administration of the nitrous oxide/oxygen mixture must be as small as possible while nevertheless providing proper delivery of the mixture to the patient and preventing escape of the mixture into the work area. Further, since nitrous oxide is continuously administered to the patient during the procedure, and the patient remains awake, slight movements of the patient are to be expected which may dislodge or cause movement of the administering mask during the procedure; such movements should not be permitted to cause significant patient/mask relative motion.

As the nitrous oxide/oxygen mixture is provided to the mask for inhalation by the patient, the escape of any such gas into the surgical work area must be prevented to avoid recognized health hazards to surgeons and staff who may be regularly exposed to such escaping gases during repeated procedures.

SUMMARY OF THE INVENTION

The present invention is directed to a mask that is both disposable and lightweight while providing appropriate delivery of the $N_2O/O_2$ mixture while also incorporating a scavenging system for the removal of exhalations of the patient. The mask is formed of a single continuous sheet of flexible disposable plastic material that is formed to conform to the shape of a patient's nose. The mask may be provided in different sizes to permit matching the mask to the patient. The mask is formed into the proper configuration for snuggly conforming to a patient's nose while incorporating a $N_2O/O_2$ nasal delivery structure and a scavenging arrangement for connection to an external exhaust system for the proper collection of exhalant and any scavenged or remaining $N_2O/O_2$.

The mask includes an adhesive surface that may be covered by release paper prior to use; the paper is removed to expose the adhesive surface to be applied to the patient's nose to stabilize and seal the mask. Preferably, the adhesive material extends from approximately the nasion to the mid dorsum and laterally to the lateral extent of the mask. The selection of an appropriate size for the specific patient enables the mask, when secured to the nose, to create a seal to control the expenditures of $N_2O/O_2$ and reduce the contamination of the work area in the vicinity of the procedure.

BRIEF DESCRIPTION OF THE DRAWINGS

The present invention may more readily be described by reference to the accompanying drawings in which:

FIG. 1 is a perspective schematic view of a patient positioned to receive a mask constructed in accordance with the teaching of the present invention.

FIG. 2 is a front view of a nasal mask constructed in accordance with the teachings of the present invention.

FIG. 3 is an interior or rear view of the mask of FIG. 2.

FIG. 4 is a cross-sectional view taken along line 4-4 of FIG. 3 useful for describing a portion of the mask constructed in accordance with the teachings of the present invention useful for describing the positioning of an input manifold.

FIG. 5 is a cross-sectional view taken along line 5-5 of FIG. 3 useful for describing a portion of the mask constructed in accordance with the teachings of the present invention useful for describing the positioning of an exhaust manifold.

FIG. 6 is a side view of a mask constructed in accordance with the teachings of the present invention shown positioned on a patient.

FIG. 7 is a cross-sectional view of a portion of FIG. 6 taken along line 7-7.

FIG. 8 is a frontal view, partly in section, of a mask constructed in accordance with the teachings of the present invention useful in illustrating the scavenging of $N_2O/O_2$ from the work area in the vicinity of the patient's mouth.

FIG. 9 is an interior view of a mask constructed in accordance with the teachings of the present invention.

DETAILED DESCRIPTION OF THE INVENTION

Figure 11:
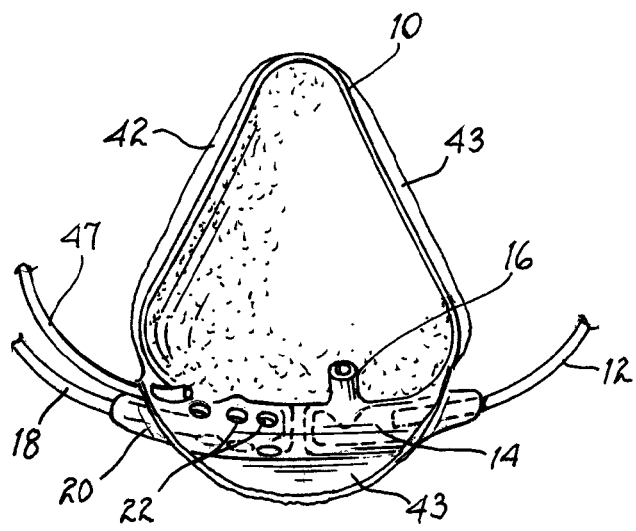
FIG. 11 is an interior view of the mask of FIG. 10.

Referring to FIG. 1, a perspective schematic view is shown of a patient having a mask, constructed in accordance with the teachings of the present invention, positioned for the appropriate administration of $N_2O/O_2$. The mask comprises a single sheet of flexible plastic material formed into a nose-conforming shell to be temporarily secured to the patient's nose during the procedure. The mask 10 is shown displaced from the patient's face for purposes of illustration; the mask 10 receives the $N_2O/O_2$ through a gas supply tube 12. The tube is connected to an appropriate regulated gas supply for proportioning the nitrous oxide and the oxygen in the mixture in accordance with the requirements of the specific procedure and the condition of the patient. The gas supply tube 12 may be a commercially available flexible tube of medical grade PVC approximately three to five mm internal diameter. The supply tube 12 delivers the $N_2O/O_2$ to the mask 10 through a manifold 14 (FIG. 4) to be directed through a prong 16 into only a single nasal vault.

A flexible vacuum tube 18 is connected to a vacuum system for the collection of exhalant from the mask and for scavenging any gasses from the work area adjacent the mask in the vicinity of the columella-labial junction. The vacuum system may be any of several commercially available systems that provide regulated vacuum levels for similar procedures. The vacuum tube 18 is connected to the mask through manifold 20 (see FIG. 5). The manifolds 14 and 20 are separated by a partition 19 to maintain separation between input gas system and output vacuum The exhaust manifold is provided with openings 21 into the interior of the mask opposite the nasal aperture for collecting exhalant and any residual $N_2O/O_2$; the exhaust manifold is also provided with passages 22 that correspond to similar passages provided in the mask 10 in the vicinity of the columella-labial area for scavenging any $N_2O/O_2$ that may have escaped from within the mask to the work area and from exhalant from the patient's mouth.

It may be noted by reference to FIGS. 4 and 5 that the sheet of flexible plastic material forming the mask 10 contacts, supports and encases the input manifold 14 and exhaust manifold 20. Supporting the respective manifolds by the flexible sheet may be accomplished through any convenient means such as adhesive, or in the event that the mask is formed using vacuum forming techniques, the sheet may be formed to sufficiently encircle the respective manifolds to secure them in place. Alternatively, in the event injection molding techniques are used in the formation of the sheet of flexible plastic forming the mask, it is possible that the sheet adjacent the manifold structures can be formed heavily enough that the friction between the respective manifolds and the mask will be sufficient to maintain the manifolds in place.

Figure 10:
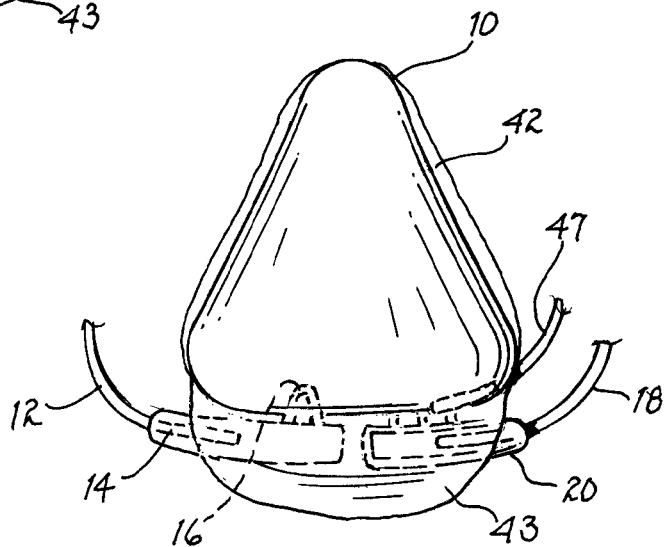
FIG. 10 is a front view of another embodiment of a mask constructed in accordance with the teachings of the present invention.

Referring to FIGS. 2 and 3, a front view and an interior or rear view respectively of the mask are shown. The scavenging or vacuum tube 18 is shown connected to the interior of the mask 10 through passages 22 formed in the exhaust manifold 20. Similarly, the gas supply tube 12 communicates to the interior of the mask through input manifold 14 and prong 16. The prong and manifold form a nasal cannula wherein the prong extends into the patient's nasal vault typically 6 to 8 mm. The mask 10 includes longitudinal flanges 42 that extend generally perpendicularly from the side walls 30 to contact the patient's face. The mask 10 includes a labial flange 43. The front wall 49 terminates in a flexible labial flange 43 as shown in FIGS. 7, 10 and 11. The flange is configured to extend from the front wall 49 adjacent the columella-labial junction into contact with and along the patient's upper lip toward the patient's mouth and lies flat against the upper lip to provide sealing contact with the patient. The labial flange 43 contacts the area of the columella-labial junction and, while flexible, is urged into contact with that area to prevent the escape of exhalant or $N_2O/O_2$ from within the mask. The flexibility of the flange permits changes in the conformation of that area during the surgical procedures while nevertheless maintaining a seal to prevent escape of gases from within the mask.

The interior surface of the mask includes an adhesive 40 that, as previously stated, may be a pressure sensitive adhesive provided with a release paper prior to application to the patient. When the release paper is removed, the mask is firmly pressed against the patient's nose and the adhesive firmly positions the mask during the subsequent procedure and forms a seal to prevent the escape of exhalant or $N_2O/O_2$ from within the mask during the procedure. The longitudinal flanges 42 may be provided with additional adhesive material; further, in some applications, it may be possible to provide adhesive material at the longitudinal flanges and adjacent peripheral portions of the mask rather than the entire mask interior. It has been found that double coated medical tape may be used as the adhesive material. For example, a transparent polyethylene medical tape available from 3M® and identified as Tape 1522, provides a double coated tape that can be applied to the interior of the mask and may conveniently be applied to the patient's nose for securely but releasably affixing the mask to the patient's nose and sealing the interior of the mask to prevent $N_2O/O_2$ from escaping the mask to the work area during the procedure.

The adhesive material may also be applied in liquid form. It has been found that application of a suitable liquid adhesive, followed by time necessary for the adhesive to become tacky, permits the positioning of the mask appropriately on the patient's nose. For example, a liquid adhesive from Torbot Group Inc. identified as Skin-Tac-H is an appropriate adhesive for application in the present invention. The adhesive is applied along the nasion dorsum to the supratip area with the adhesive distributed on the interior surfaces of the mask shell.

Referring to FIGS. 6 and 7, a side view of a mask positioned on a patient is shown together with a cross-section thereof to illustrate the positioning of the mask on the patient's nose. The mask shown includes the adhesive contact between the mask and the patient's nose from approximately the nasion dorsum to the supra tip area. The mask extends along the nasion dorsum and is positioned to provide a chamber 45 that may, for example, measure approximately 6 mm from the columella to the front wall 49 of the mask at the nose tip and extend caudally from the tip to the base at the columella-labial junction. This chamber 45 provides a volume within which the exhalant and any residual $N_2O/O_2$ is scavenged or removed through the vacuum tube.

FIGS. 8 and 9 are further views of a mask constructed in accordance with the teachings of the present invention and are useful in illustrating the scavenging of $N_2O/O_2$ from the work area in the vicinity of the patient's mouth and externally of the mask. The scavenging of such gases from the work area is an important health consideration for surgeons and staff that may be exposed to such gas on an intermittent basis over a prolonged period of time through several procedures.

Referring to FIGS. 10 and 11, another embodiment of the present invention is shown incorporating a means for conveniently monitoring a patient's carbon dioxide exhalant during the procedure. FIGS. 10 and 11 are respectively a front elevation and an interior or rear elevation view of another embodiment of a mask constructed in accordance with the teachings of the present invention. The mask is shown having longitudinal flanges 42 and the labial flange 43. The exhaust manifold 20 and corresponding exhaust or vacuum tube 18 are shown as previously described. Similarly, the input manifold 14 and gas supply tube 12 are shown together with the prong 16 that extends into only a single nasal vault of the patient. The mask may be supplied with an adhesive 40 as previously described. In addition to the supply tube 12 and vacuum or exhaust tube 18, a carbon dioxide monitoring tube 47 extends into the interior of the mask and is positioned within the chamber 45. The carbon dioxide monitoring tube end 47 is positioned opposite the nasal aperture of the patient; the positioning is opposite the nasal vault not containing the gas-supplying prong 16. That is, the monitoring tube 47 terminates in the vicinity of the likely maximum exhalant flow during expiration. The exhalant is transported via the carbon dioxide monitoring tube 47 to commercially available equipment for measurement as an indicator of ventilation. It has been proposed that carbon dioxide monitoring as an indicator of ventilation is a superior process for proper indication of sedated states or relaxation states of patients. The carbon dioxide monitoring tube 47 is connected to a carbon dioxide monitoring apparatus of the type presently available; however, the volume and rate of flow of the exhalant in the tube 47 is determined by the requirements of carbon dioxide monitoring system; therefore, the monitoring tube 47 is independent of the vacuum system and vacuum tube 18. That is, the carbon dioxide monitoring system operates independently, although incorporated in the mask of the present invention, and will supply its monitoring equipment with the appropriate volume and rate of flow.

The small size, lightweight, and proper fitting of the mask of the present invention permits the utilization of a smaller supply of gases. Since the delivery of gases and the scavenging of the gases are directed to a small chamber that is positioned closely to the patient's nasal aperture, the gases can be directed specifically to the patient with less leakage—less $N_2O/O_2$ is used with the same therapeutic effect. Importantly, as previously described, gas leakage and contamination of the vicinity of the procedure has been shown to be deleterious to the dental/surgical team present during the procedure. Long term exposure to such leaked nitrous oxide gases gas present serious health hazards.

The small lightweight size of the present mask and the small tubings that permit appropriate supply of nitrous gas/oxygen mixture as well as the smaller tube thus required for scavenging, permits the tubes to extend from the mask in the vicinity of the chamber 45 generally toward the patient's ears to thereby facilitate positioning of the tubes conveniently upwards over the patient's ears. The lightweight tubing is unobstructive and presents less pressure to the patient then ordinary eyeglass arms. The small size of the mask positioned and secured as described above exposes the upper lip and remains in a non-interfering position throughout the procedure. The small size of the mask permits the patient to wear protective eyewear during the procedure. That is, the patient may wear standard eyewear that is conventionally worn during dental and surgical procedures to prevent inadvertent eye injuries; the mask, and connected tubes, are non-interfering and permit the common and comfortable placement of protective eyewear during the procedures. The accommodation of such eyewear is not possible with presently available and prior art nasal masks. The lightweight mask of the present invention also reduces patient stress and discomfort and can reduce sensations of claustrophobia. The disposability of the mask reduces possibilities of disease transmission and can more easily be managed by the professional staff in the positioning and administration of the mask before and during a procedure.

It has been found that a sheet of flexible plastic material of ethylene-vinyl acetate, having a thickness of 0.040" from Henry Schein® and identified as Mouthguard Thermo-Forming 101-8910 is suitable for the formation of the mask. This sheet of material was vacuum formed over a model of a patient's nose with the input manifold and exhaust manifolds encased and appropriately positioned with respect to the nose to conform to the above described relationship. The resulting mask, with the cannula formed by the manifold and the nasal prong, included the labial flange and incorporated the longitudinal flanges described above. An adhesive surface was supplied as described above. The resulting structure was admirably suited to the intended purpose and, when secured to patients as described and connected to commercially available $N_2O/O_2$ supply and vacuum sources, provided appropriate gas administration to patients through the input or gas supply tube and nasal prong while providing exhaust collection and scavenging through the connected vacuum tube.

The present invention has been described in terms of selected specific embodiments of the apparatus and method incorporating details to facilitate the understanding of the principles of construction and operation of the invention. Such reference herein to a specific embodiment and details thereof is not intended to limit the scope of the claims appended hereto. It will be apparent to those skilled in the art that modifications may be made in the embodiments chosen for illustration without departing from the spirit and scope of the invention.

What is claimed:

1. A nasal masking system for use with oral or facial surgery or dental procedures and for supplying nitrous oxide/oxygen gas mixture to a patient, comprising:
   (a) flexible plastic material formed into a nose conforming shell and having sidewalls, a front wall and an interior and an exterior;
   (b) said shell configured to extend along a patient's nose from the nasion dorsum to the supra tip and to the columella-labial junction and including an extension of the front wall forming a flexible labial flange extending from said front wall configured to contact the patient's upper lip in the columella-labial area, said flange, when the mask is in place, forming a flexible seal;
   (c) an adhesive positioned on the interior surface of said interior configured to extend from the patient's nasion to the mid dorsum and laterally to the extent of the mask to be pressed against the patient's nose to position the mask and maintain the position during a procedure;
   (d) an input manifold within said nose conforming shell, for connection to a source of regulated gas mixture for delivering said gas to one of a patient's first and second nasal vaults, said input manifold configured to be positioned adjacent the patient's columella-labial junction, said input manifold including a gas supplying prong positioned to extend into only said first nasal vault of the patient for delivering the gas mixture through said prong and first nasal vault to the patient, no gas supplying prong is provided for the second nasal vault; and
   (e) an exhaust manifold within said nose conforming shell configured to be positioned adjacent the patient's columella-labial junction for connection to a source of vacuum, and having an opening to the interior of said shell positioned opposite only the second nasal vault with no opening opposite the first nasal vault of the patient, for collecting exhalant, and having scavenging openings in said exhaust manifold communicating with the exterior of said shell-adjacent said flexible labial flange and configured to be adjacent the patient's columella-labial area for scavenging any gas mixture that may have escaped from within the shell in the columella-labial area and to collect escaped gases and direct said gases directly into said exhaust manifold without traversing the interior of said shell;

whereby, said gas mixture is supplied to a patient through the input manifold within a nose conforming mask exclusively through a first nasal vault, and exhalant is removed exclusively through a second nasal vault through openings in the exhaust manifold positioned opposite said second nasal vault.

2. The nasal masking system of claim 1 including a supply tube extending from said input manifold and a vacuum tube extending from said exhaust manifold, said supply tube and vacuum tube configured to extend from said input manifold and exhaust manifold, respectively, toward and be supported by a patient's ears.

3. The nasal masking system of claim 1 wherein said labial flange is configured to extend from said front wall into contact with and along a patient's upper lip toward the patient's mouth and lie flat against the upper lip.

4. A nasal mask system for use with oral or facial surgery or dental procedures, comprising:
   (a) flexible plastic material formed into a nose conforming shell and having sidewalls, a front wall and an interior and an exterior;
   (b) said shell configured to extend along a patient's nose from the nasion dorsum to the supra tip and to the columella-labial junction and including flexible longitudinal flanges extending substantially perpendicularly from said sidewalls and configured to contact a patient's face, and an extension of the front wall forming a flexible labial flange configured to contact the patient's upper lip in the columella-labial area, said flanges, when the mask is in place, forming flexible seals;
   (c) an adhesive positioned on the interior surface of said interior configured to extend from the patient's nasion to the mid dorsum and laterally to the extent of the mask to be pressed against the patient's nose to position the mask and maintain the position during a procedure;
   (d) a manifold encased within said nose conforming shell adjacent the columella-labial junction and having a partition therein to form an input manifold and an opposing exhaust manifold for connection to a source of regulated gas mixture and to a source of vacuum, respectively;
   (e) said input manifold including a gas supplying single prong positioned to extend into only a first nasal vault of a patient for delivering $N_2O/O_2$ gas mixture to the patient, no gas supplying prong is provided for the second nasal vault; and
   (f) said exhaust manifold having an opening positioned opposite a second nasal vault of the patient for collecting exhalant and having openings configured to communicate with the exterior of said shell adjacent the patient's columella-labial area for scavenging any gas mixture that may have escaped from within the shell in the work area adjacent the mask in the columella-labial area;

whereby, said gas mixture is supplied to a patient through the input manifold and the prong extending into a first nasal vault, and exhalant is removed through a second nasal vault through openings in the exhaust manifold positioned opposite said second nasal vault.

5. The nasal mask system of claim 4 including a supply tube extending from said input manifold and a vacuum tube extending from said exhaust manifold, said supply tube and vacuum tube configured to extend from said input manifold and exhaust manifold, respectively, toward and be supported by a patient's ears.

6. The nasal masking system of claim 4 wherein said labial flange is configured to extend from said front wall into contact with and along a patient's upper lip toward the patient's mouth and lie flat against the upper lip.

\* \* \* \* \*